United States Patent [19]

Cortial

[11] Patent Number: 4,857,199

[45] Date of Patent: Aug. 15, 1989

[54] METHOD AND SYSTEM FOR PUMPING TWO LIQUIDS IN EQUAL QUANTITIES IN AN ARTIFICIAL KIDNEY

[75] Inventor: Jean-Loup Cortial, Lyon, France

[73] Assignee: Hospal Industrie, Cedex, France

[21] Appl. No.: 110,347

[22] Filed: Oct. 20, 1987

[30] Foreign Application Priority Data

Oct. 20, 1986 [FR] France ............................... 86 14849

[51] Int. Cl.$^4$ .............................................. B01D 13/00
[52] U.S. Cl. ..................................... 210/646; 210/101;
210/321.65; 210/321.71; 210/321.72; 210/650;
210/739; 210/929
[58] Field of Search .............. 210/101, 321.65, 321.71,
210/321.72, 646, 647, 650, 739, 929

[56] References Cited

U.S. PATENT DOCUMENTS 4,054,522 10/1977 Pinkerton ........................ 210/321.71
4,477,342 10/1984 Allan et al. ........................... 210/929
4,728,433 3/1988 Buck et al. ..................... 210/321.71

FOREIGN PATENT DOCUMENTS 2634238 2/1978 Fed. Rep. of Germany .

Primary Examiner—W. Gary Jones
Attorney, Agent, or Firm—Finnegan, Henderson, Farabow, Garrett and Dunner

[57] ABSTRACT

A method and a system of pumping a first and a second liquid in an artificial kidney in substantially equal quantities at a substantially constant flow. The system includes a main pump having complementary main chambers, and first and second auxiliary pumps each having complementary auxiliary chambers. The pumps are reciprocated in unison and the system further includes a unique configuration of intake and discharge lines and associated control valves which provide a constant and equal flow of first and second liquid into and out of the artificial kidney during reciprocation of the pumps in both directions.

21 Claims, 7 Drawing Sheets

METHOD AND SYSTEM FOR PUMPING TWO LIQUIDS IN EQUAL QUANTITIES IN AN ARTIFICIAL KIDNEY

BACKGROUND OF THE INVENTION

1. Field of the Invention

The present invention relates to artificial kidneys, and more particularly, to a method and system for pumping two liquids in equal quantities and with a continuous flow rate in two separate conduits of an artificial kidney.

2. Description of the Related Art

Artificial kidneys typically pump two liquids, for example, fresh and used dialysis liquid, into and out of a hemodialyser. An example of a known apparatus for pumping the two liquids is illustrated in FIG. 1 and includes, a pumping device 106 having two complementary chambers 112 and 113 associated with four valves 126, 127, 128 and 129, disposed, respectively, in lines 118, 119, 121 and 120. The operation of such a device is effected over two periods. During the first period, the valves 126 and 127 are closed, and valves 128 and 129 are open. A reciprocating piston 109, separating the two complementary chambers 112 and 113, is moved in direction A so as to aspirate a first liquid into chamber 112, and, at the same time, discharge an equal quantity of a second liquid from chamber 113. In the second period, valves 128 and 129 are closed, and valves 126 and 127 are open, and piston 109 is moved in direction R to discharge from chamber 112 a quantity of the first liquid into line 118, and to simultaneously aspirate a quantity of the second liquid into chamber 113 from line 119.

With the device depicted in FIG. 1, it is possible to pump two liquids in substantially equal quantities in two separate conduits, but the flows in the four lines 118, 119, 120 and 121, are discontinous due to the alternating movement of piston 109 during reciprocation.

To mitigate this drawback, apparatus have been proposed which, effectively, comprise two of the devices of FIG. 1 arranged in parallel. Such a system is illustrated in FIG. 2 and includes two pumping devices 206 and 206' having respective complementary chambers 212, 213 and 212', 213' associated with eight valves 226, 226'; 227, 227'; 228, 228'; and 229, 229', disposed in respective conduits or lines connected to the chambers of pumping devices 206 and 206' as shown.

Operation of the device of FIG. 2 is as follows. In a first period, valves 226, 227, 228' and 229' are closed; and valves 228, 229, 226' and 227' are opened. A pair of reciprocating pistons 209 and 209', disposed in pumps 206 and 206', respectively, are then moved in direction A. Movement of piston 209 in direction A aspirates the first liquid into chamber 212 from an intake line 220, and discharges the second liquid from chamber 213 into an outlet line 221. Simultaneously, movement of piston 209' in direction A, discharges the first liquid from chamber 213' into an outlet line 218, and aspirates the second liquid into chamber 212' from an intake line 219.

In a second period, valves 226, 227, 228' and 229' are opened, and valves 228, 229, 226' and 227' are closed. Reciprocating pistons 209 and 209' are then moved in direction R. Piston 209' upon being moved in direction R, aspirates the first liquid into chamber 213', and discharges the second liquid from chamber 212' into line 221. Simultaneously, movement of the piston 209 in direction R aspirates the second liquid into chamber 213 from line 219, and discharges the first liquid from chamber 212 into line 218.

By means of systems such as illustrated in FIG. 2, substantially continuous flow through lines 218, 219, 220, 221 can be attained.

A system similar to the one described above with reference to FIG. 2 is described in German Patent Application DOS 2 634 238. However, the embodiments of the device disclosed in that German patent utilize elastic members disposed in respective chambers rather than reciprocating pistons. The circulation of the fresh and used dialysis liquid comprising the first and second liquids is accomplished by two pumps displacing the membranes in the chambers to displace the dialysis liquid.

In principle, these prior art systems allow two liquids in two separate conduits to be pumped in substantially equal quantities and with a substantially continuous flow. However, small errors occur each time the valves (226, 227, 228, 229, 226', 227', 228', 229') are opened or closed. With a high frequency of opening and closing of the valves, the accumulation of these small errors leads to an even higher overall error.

It is therefore an object of the present invention to provide a method and an apparatus for pumping equal quantities of two liquids through two separate conduits in which the errors associated with the valves opening and closing are substantially reduced.

Additional objects and advantages of the invention will be set forth in the description which follows, and in part will be obvious from the description, or may be learned by practice of the invention. The objects and advantages of the invention may be realized and attained by means of the instrumentalities and combinations particularly pointed out in the appended claims.

SUMMARY OF THE INVENTION

A system is provided for pumping a predetermined quantity of a first liquid from a source through the outlet of a discharge line to be attached to an appliance such as a hemodialyser of an artificial kidney, and for pumping the same quantity of a second liquid from an intake line inlet into evacuation means, with both liquids moving at a substantially equal and constant flow. The system comprises a main reciprocating pump means having first and second complementary main chambers, and first and second auxiliary reciprocating pump means. The first auxiliary pump means has first and second complementary auxiliary chambers, and the second auxiliary pump means has third and fourth complementary auxiliary chambers. A drive means is provided for reciprocating the main pump means and the first and second auxiliary pump means in unison between a first and second direction such that the volume of the first main chamber varies inversely with the volume of the second and fourth auxiliary chambers, and directly with the volume of the first and third auxiliary chambers.

A first intake line means is provided for aspirating the predetermined quantity of the first liquid into the first main chamber from both the fourth auxiliary chamber and from a source of the first liquid during reciprocation of the pump means in the first direction, and for aspirating the quantity of the first liquid into the fourth auxiliary chamber from the source of the first liquid during reciprocation of the pump means in the second direction. A first discharge line means is provided for discharging the quantity of the first liquid into both the second auxiliary chamber and into a discharge line outlet during reciprocation of the pump means in the second direction, and for discharging the quantity of the first liquid into a discharge line outlet from the second auxiliary chamber during reciprocation of the pump means in the first direction.

A second intake line means is provided for aspirating the quantity of the second liquid into the second main chamber from both an intake line inlet and the third auxiliary chamber during reciprocation of the pump means in the second direction, and for aspirating the quantity of the second liquid into the third auxiliary chamber from an intake line inlet during reciprocation of the pump means in the first direction. A second discharge line means is provided for discharging the quantity of the second liquid into both the first auxiliary chamber and a drain during reciprocation of the pump means in the first direction, and for discharging the quantity of the second liquid into the drain from the first auxiliary chamber during reciprocation of the pump means in the second direction. The above described system operates such that the same quantity of the first and second liquid moves in a substantially constant flow during reciprocation of the pump means in both the first and the second direction.

BRIEF DESCRIPTION OF THE DRAWINGS

The accompanying drawings, which are incorporated in and constitute a part of the specification, illustrate a presently preferred embodiment and method of the invention and, together with the general description given above and the detailed description of the preferred embodiment and method given below, serve to explain the principles of the invention.

DESCRIPTION OF THE PREFERRED EMBODIMENTS

Reference will now be made in detail to the present preferred embodiments and method of the invention as illustrated in the accompanying drawings.

Figure 1:
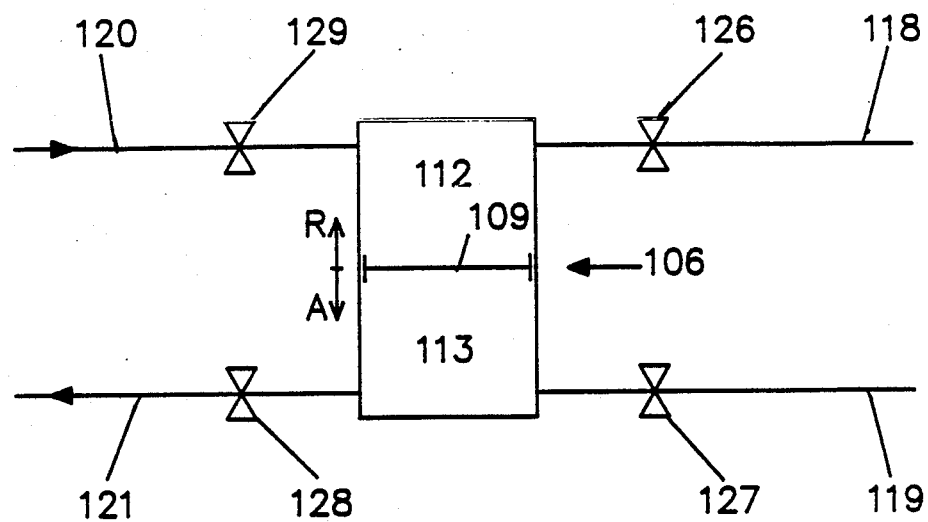
FIG. 1 illustrates schematically a prior art pumping device having two complementary chambers associated with four valves.
Figure 2:
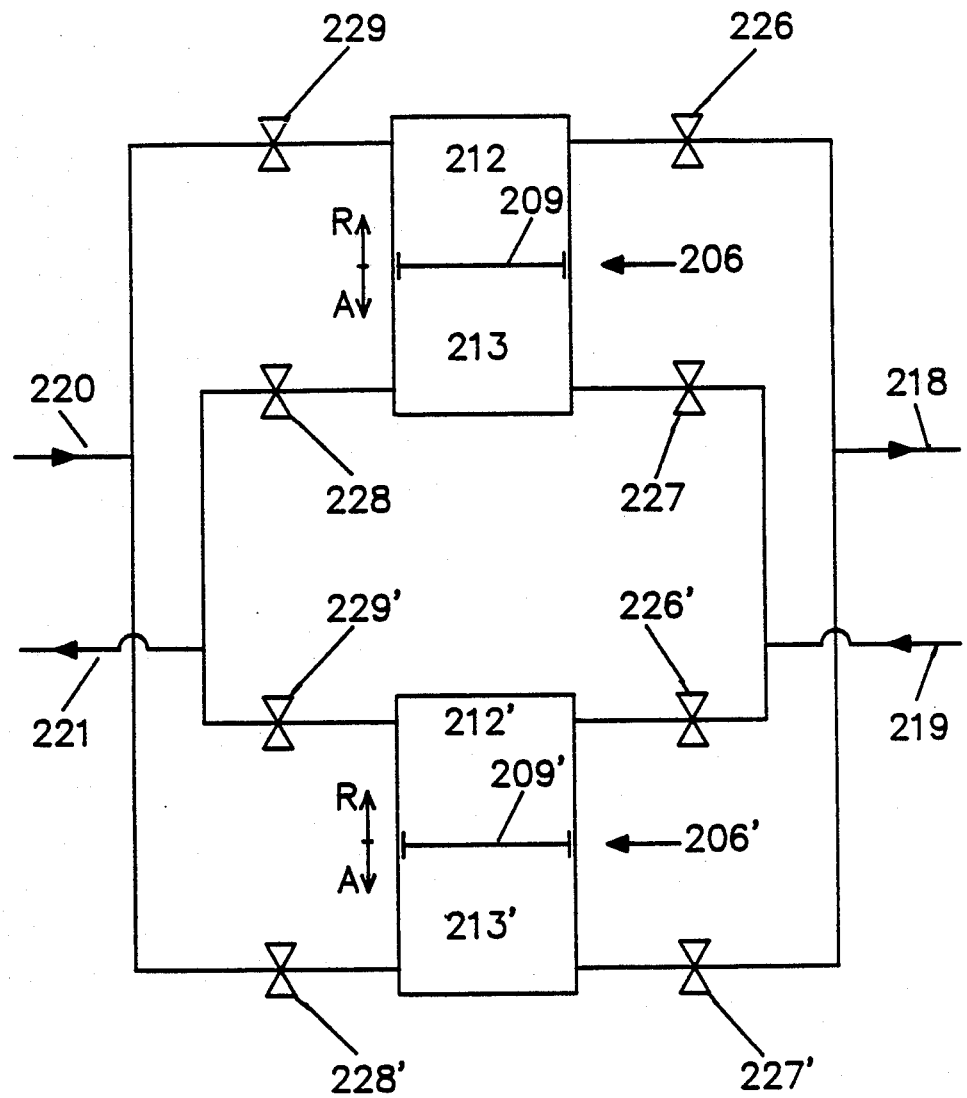
FIG. 2 illustrates schematically a second prior art device essentially incorporating two of the devices illustrated in FIG. 1 disposed in parallel.
Figure 3:
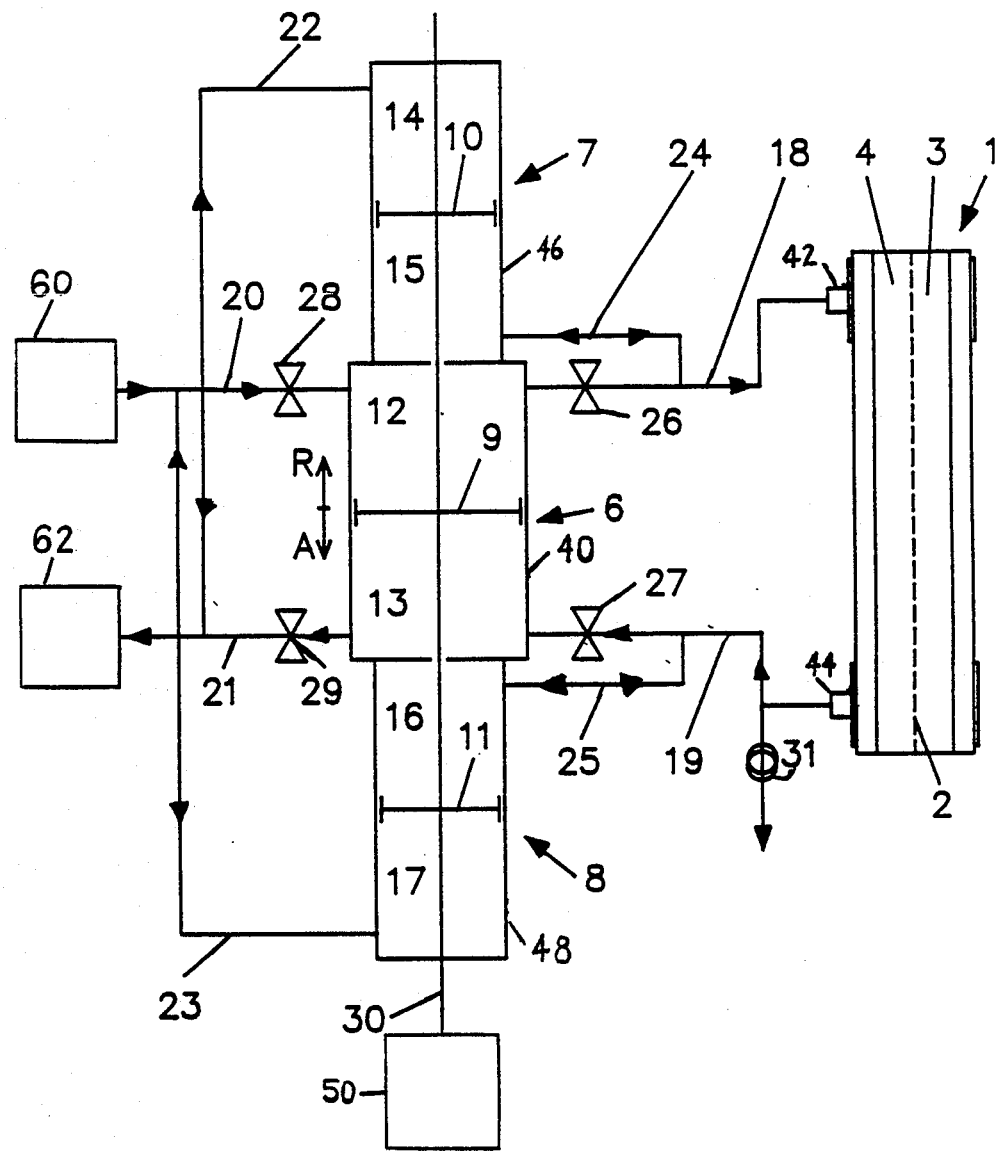
FIG. 3 schematically illustrates a first embodiment of the present invention applied to pumping dialysis liquid in an artificial kidney.

In accordance with the present invention, and as illustrated in FIG. 3, there is provided pumping system for an artificial kidney. As embodied herein, the pumping system is hooked to a hemodialyser 1 separated into two compartments 3 and 4 by a semi-permeable membrane 2 permitting dialysis and ultrafiltration of the blood. First compartment 3 is intended for the extracorporeal circulation of the blood, and second compartment 4 is intended for the circulation of the dialysis liquid flowing from a source 60, into the hemodialyser, then from the hemodialyser towards an evacuation means 62. As embodied herein, evacuation means 62 may include regeneration means.

In accordance with the invention the system includes a main reciprocating pump means and first and second auxiliary reciprocating pump means. As embodied herein, the main pump means comprises a main pump 6, and the first and second auxiliary pump means includes auxiliary pumps 7 and 8, respectively. Main pump 6 comprises a cylinder 40 which is separated into complementary first and second main chambers 12 and 13 by a piston 9. Each auxiliary pump 7 and 8 includes a cylinder 46 and 48, respectively, which are separated into first, second, third, and fourth auxiliary chambers 14, 15, 16, and 17, respectively, by a piston 10 disposed in cylinder 46 and a piston 11 disposed in cylinder 48. Each of the pistons is tightly sealed about its periphery in its respective cylinder. In the present preferred embodiment of the invention, pistons 10 and 11 are coaxial and fixedly connected to one another, and to main piston 9, by a rod 30. A drive means, which will be described hereinafter, is connected to rod 30 to move pistons 9, 10 and 11 in unison in a reciprocating motion between directions A and R.

Main chamber 12 of pump 6 holds the fresh dialysis liquid and is connected to dialysis liquid source 60 and to fourth auxiliary chamber 17 by a first intake line means. As embodied herein, the first intake line means includes lines 20 and 23 and valve means 28 disposed in line 20.

Main chamber 12 is also connected to an inlet 42 of hemodialyser 1 and to second auxiliary chamber 15 by a first discharge line means, which, as embodied herein comprises lines 18 and 24, and valve means 26 disposed in line 18.

Main chamber 13 holds the used dialysis liquid and is connected to an outlet 44 of hemodialyser 1 and to third auxiliary chamber 16 by a second intake line means, which, as embodied herein comprises lines 19 and 25, and valve means 27 disposed in line 25. Main chamber 13 is also connected to an evacuation or regeneration means 62 for the used dialysis liquid and to first auxiliary chamber 14 by a second discharge line means, which, as embodied herein, comprises lines 21 and 22, and valve means 29 disposed in line 21.

In each auxiliary pump 7 and 8, second and fourth auxiliary chambers 15 and 17 cycle fresh dialysis liquid, and first and third auxiliary chambers, 14 and 16, cycle the used dialysis liquid.

Auxiliary chamber 14 is connected to line 21 downstream of valve means 29 by line 22. Auxiliary chamber 15 is connected to discharge line 18 downstream of valve means 26 by line 24. Auxiliary chamber 16 is connected to output line 19 upstream of valve means 27 by line 25. Auxiliary chamber 17 is connected to intake line 20 upstream of valve means 28 by line 23.

Auxiliary chambers 14 and 16 regulate the flow of the used dialysis liquid, while auxiliary chambers 15 and 17 regulate the flow of the fresh dialysis liquid. The design of pumps 6, 7 and 8 is selected such that simultaneous displacement of the pistons disposed therein displaces a quantity of liquid in each main chamber 12 and 13 which is twice the quantity of liquid displaced in each auxiliary chamber 14, 15, 16 and 17. In the case where pumps 6, 7, and 8 have a circular cross section, auxiliary pumps 7 and 8 may be configured with a cross section equal to half the cross section of main pump 6.

Operation of the apparatus illustrated schematically in FIG. 3 is discussed below. Rod 30 is connected to each piston 9, 10 and 11 and is driven in a rectilinear reciprocating motion by any type of suitable motor or drive menas schematically represented by 50 to reciprocate pistons 9, 10 and 11 between a first direction represented by arrow A, and a second direction represented by arrow B.

In a first stage called the aspiration stage, valve means 26 and 27 are closed, and valve means 28 and 29 are open. Rod 30 is driven such that pistons 9, 10 and 11 are displaced in the direction of arrow A. The displacement of the pistons in direction A draws fresh dialysis liquid into chamber 12 and ejects used dialysis liquid from chamber 13. One half of the dialysis liquid drawn into chamber 12 comes from the source of fresh dialysis liquid 60, through line 20 and valve 28, and one-half of the fresh dialysis liquid drawn into chamber 12 comes from auxiliary chamber 17 via lines 23, 20 and valve 28.

With movement of pistons 9, 10 and 11 still in direction A, one-half of the dialysis liquid discharged from chamber 13 is drawn into auxiliary chamber 14 via lines 21, 22 and valve 29 by simultaneous displacement of pistons 9 and 10; and the other half of the dialysis liquid is discharged through line 21 and valve 29 to evacuation or regeneration means 60. Displacement of piston 10 in direction A simultaneously delivers the fresh dialysis liquid from auxiliary chamber 15 to hemodialyser 1 via lines 24 and 18 since valve 26 is closed. Displacement of the piston 11 in direction A aspirates used dialysis liquid from hemodialyser 1 into auxiliary chamber 16 via lines 19 and 25 since valve 27 is closed.

In a second stage called the delivery stage, rod 30 is driven such that pistons 9, 10 and 11 are displaced in the direction of arrow R. Valve means 26 and 27 are open, and valve means 28 and 29 are closed.

The decrease in volume of main chamber 12 by movement of piston 9 in direction R aspirates equal quantities of fresh dialysis liquid into auxiliary chamber 15 via lines 18, 24 and valve 26 on the one hand, and on the other hand, into hemodialyser 1 through line 18, valve 26, and first discharge line outlet 42. The increase in volume of chamber 13 and decrease in volume of chamber 16 by movement of pistons 9 and 11 in direction R aspirates used dialysis liquid into chamber 13 via outlet line 19 and valve 27 from hemodialyser 1, and from chamber 16 into chamber 13 via lines 19, 25 and valve 27.

In effect, the movement of pistons 9, 10 and 11 in direction R discharges used dialysis liquid from auxiliary chamber 16 and simultaneously aspirates fresh dialysis liquid into auxiliary chamber 17 via line 20 and line 23. At the same time, used dialysis liquid from auxiliary chamber 14 is discharged into line 21 from chamber 14 via line 22.

The successive closing and opening of the valve means 26, 27, 28 and 29 in the sequence described above, as well as the change in the direction of displacement of rod 30 and pistons 9, 10 and 11, may be actuated by means of end of travel contacts integral with rod 30 and associated with a guidance system (not shown) of any known type, such as a microprocessor for controlling the sequential opening and closing of the valves.

Figure 4:
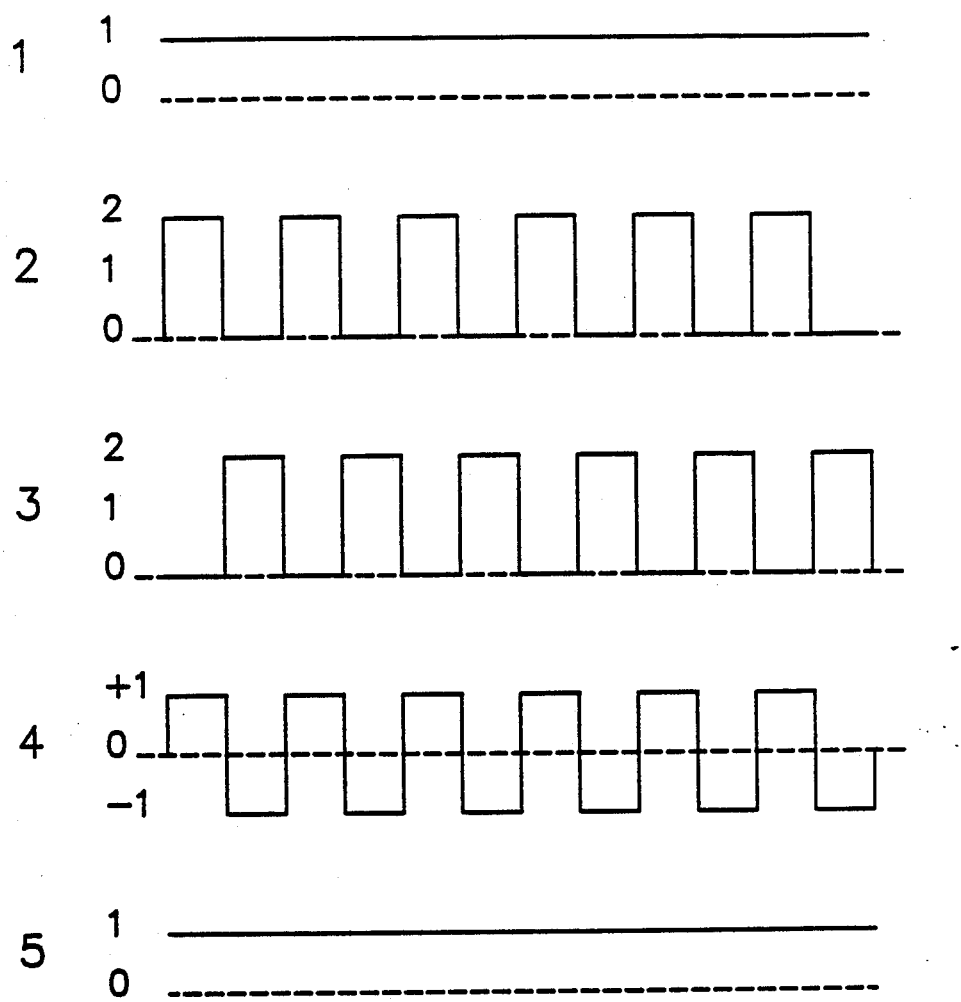
FIG. 4 graphically illustrates variations of flow with respect to time for a first liquid being pumped through the embodiment of the present invention illustrated in FIG. 3.
Figure 5:
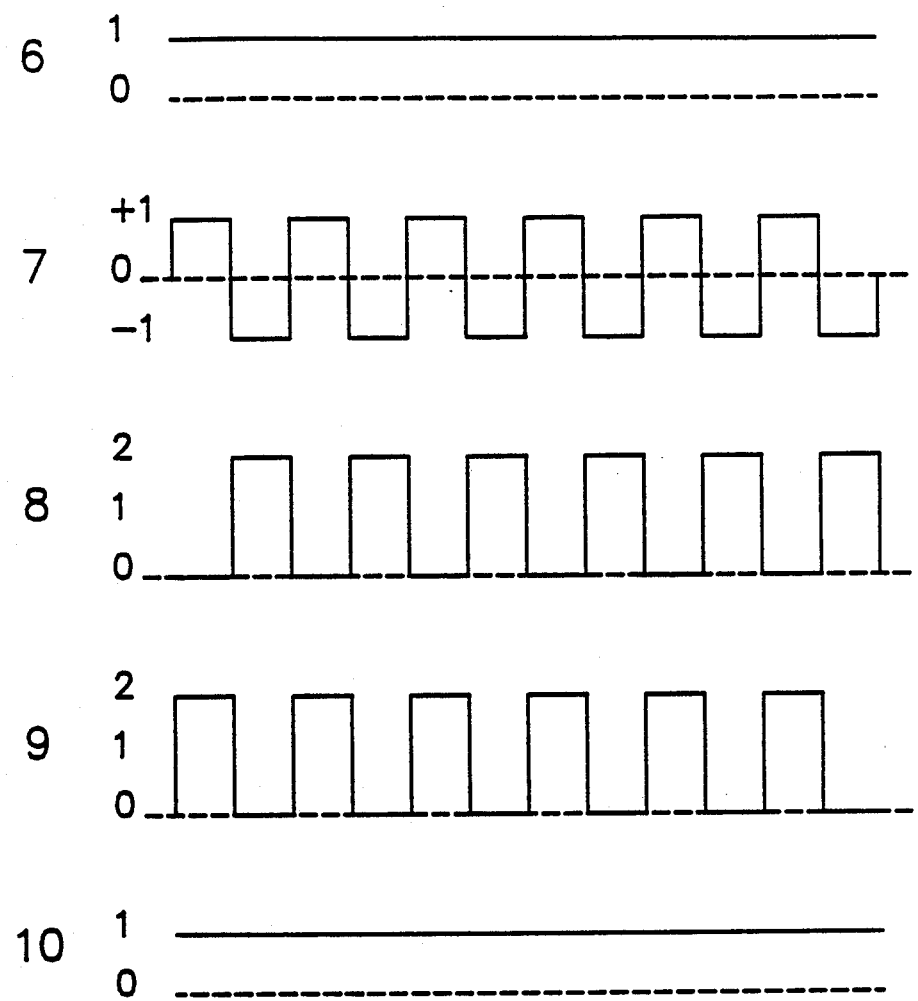
FIG. 5 graphically illustrates variations of flow with respect to time for a second liquid being pumped through the embodiment of the present invention illustrated in FIG. 3.

With reference to the graphs of FIGS. 4 and 5 illustrating the flows in the various lines, it will, on the one hand, be observed that the quantity of the fresh dialysis liquid, or first liquid, drawn into respective chambers is equal to the quantity of the used dialysis liquid, or second liquid, delivered into respective chambers by the pumping system according to the present invention, and, on the other hand, that the flows of the dialysis liquid are continuous in the lines 18 and 19, that is to say, at outlet 42 and at inlet 44.

All the graphs illustrated in FIGS. 4 and 5 indicate time on the x axis subdivided into successive aspiration and delivery stages of the system, and the flow, expressed in units of flow 0, +1, −1, and 2 on the y axis. For example, one may choose a flow unit to be equal to 500 ml/min.

The graphs lines of FIG. 4 correspond to the variations of flow in the lines which deliver fresh dialysis liquid to hemodialyser 1, and the graph lines of FIG. 5 correspond to the variations of flow in the corresponding lines which expel the used dialysis liquid.

Graph line 1 of FIG. 4 represents flow through line 20 upstream of the junction with line 23 and shows that the supply of fresh dialysis liquid is effected at a constant flow rate. Regardless of whether the system is in the aspiration stage or in the delivery stage, there is always one unit of flow in line 20 upstream from the junction with line 23. This unit of flow is delivered alternately, in accordance with the direction pistons 9 and 11 are moved, to either first main chamber 12 or fourth auxiliary chamber 17, depending on whether valve 28 is open or closed.

The graph line 2 represents the circulation in line 20 downstream from the junction with line 23. It will be seen that when valve 28 is open, that is to say, in the aspiration stage with pistons 9, 10 and 11 moved in direction A, the flow rate of the dialysis liquid is two units, one unit coming from auxiliary chamber 17 via line 23, and one unit coming from the dialysis liquid source 60. In the delivery stage of the apparatus, that is, movement of pistons 9, 10 and 11 in direction R, the flow in line 20 is zero since valve 28 is closed.

On the other hand, in graph line 3, it is seen that in line 18 upstream of the junction with line 24, the flow rate is zero in the aspiration stage since valve 26 is closed, and is equal to two units in the delivery stage with valve 26 open. The two units of flow in line 18 during the delivery stage are supplied from main chamber 12 as piston 9 moves in direction R. One unit of flow is delivered to auxiliary chamber 15 through line 24, and one unit is delivered through first discharge line outlet 42.

The graph line 4 represents the flow rate in line 24. In the aspiration stage, the flow rate is a positive one unit, that is to say, the dialysis liquid flows from chamber 15 towards line 18 since valve 26 is closed, while in the delivery stage, the flow rate is a negative one unit in line 24, the negative signifying that the liquid then flows from first main chamber 12 through lines 18 and 24 into auxiliary chamber 15 with valve 26 open.

The graph line 5 represents the flow rate of the dialysis liquid that passes through first discharge line outlet 42. It may be considered as the sum of the flow rates of the graph lines 3 and 4. It will then be seen that the flow rate at outlet 42 is continuous and equal to the flow provided by the source of the fresh dialysis liquid. During movement of pistons 9, 10 and 11 in direction R, one unit of flow is delivered to first discharge line outlet 42 from first main chamber 12, and during movement of the pistons in direction A, one unit of flow is delivered to outlet 42 from second auxiliary chamber 15.

Referring to the graph line 6 of FIG. 5, it will be seen that the flow rate of the used dialysis liquid through inlet 44 of second intake line 19 from the hemodialyser, upstream from the junction of line 25 is continuous and equal to one unit. This flow may be considered to be the sum of the flows of the graph line 7 and of graph line 8 described below.

The graph line 7 represents the flow rate of the dialysis liquid in line 25. In the aspiration stage, that is, movement of the pistons in direction A, the flow rate is a positive one unit, that is the liquid flows from inlet 44 through line 19 towards auxiliary chamber 16 since valve 27 is closed, while in the delivery stage the flow rate is a negative one unit, that is, the liquid flows from auxiliary chamber 16 into main chamber 13 since valve 27 is open.

The graph line 8 represents the flow rate in line 19 downstream from the junction with line 25. In the aspiration stage, that is to say when the valve 27 is closed and the pistons are moved in direction A, the flow rate is zero; and in the delivery stage, that is to say when the valve 27 is open and the pistons are moved in direction R, the flow rate is equal to two units, one unit coming from auxiliary chamber 16 via line 25 and one unit coming from hemodialyser 1 through line 19.

The graph line 9 represents the flow rate in line 21 upstream from the junction with line 22. In the aspiration stage, that is to say when the valve 29 is open, the flow rate is equal to two units delivered from first main chamber 13 as piston 9 moves in direction A. In the delivery stage, that is to say when the valve 29 is closed, the flow rate is zero.

The graph line 10 represents the flow rate in line 21 downstream from the junction with the line 22, this is, the flow of the used dialysis liquid directed to the evacuation or regeneration means 62. The flow rate in line 21 downstream of the junction with line 22 is continuous and equal to 1 unit. During movement of pistons 9, 10 and 11 in direction A with valve 29 open, one unit is delivered from main chamber 13, and during movement of the pistons in direction R with valve 29 closed, one unit is delivered from first auxiliary chamber 14.

A comparison of the graph lines 1 and 10 shows that the quantity of liquid entering the system through line 20 is equal to the quantity of liquid emerging from the system through line 21. Furthermore, the graph lines 5 and 6, representing the circulation of the dialysis liquid in lines 18 and 19, respectively, demonstrate that the dialysis liquid passes through hemodialyser 1 in a continuous flow.

The quantity of the dialysis liquid drawn in and delivered during each successive aspiration and delivery stage depends on the amplitude or stroke of piston 9. The total quantity of the dialysis liquid passing through the circuit during the treatment session as a whole, depends on the value of the flow rate and hence on the frequency of the aspiration and delivery stages, that is to say, on the speed at which the rod 30 is driven.

With continued reference to FIG. 3, an ultrafiltration pump 31 may be provided to draw off a quantity of dialysis liquid which is equal to the quantity of liquid which one wishes to eliminate from the patient's blood by ultrafiltration.

In fact, in the case where the dialysis liquid circuit is a non-deformable, closed circuit, any quantity of liquid withdrawn from the dialysis liquid circuit produces a low pressure in the circuit which creates a pressure gradient at the level of the hemodialyser on either side of membrane 2. This pressure gradient causes a quantity of ultrafiltrate from the patient's blood to pass across semi-permeable membrane 2 of hemodialyser 1. This quantity of ultrafiltrate is equal to the quantity of liquid withdrawn from the dialysis liquid circuit.

The dialysis liquid can be withdrawn from line 19, upstream from the junction with line 25, as represented in FIG. 3, but may also be withdrawn from line 18 downstream from the junction with line 24.

Although not represented in the drawings, provision may moreover be made in the dialysis liquid circuit for degassing devices, pressure transducers or flow detectors or any other accessory which is non-critical as far as the present invention is concerned.

Figure 6:
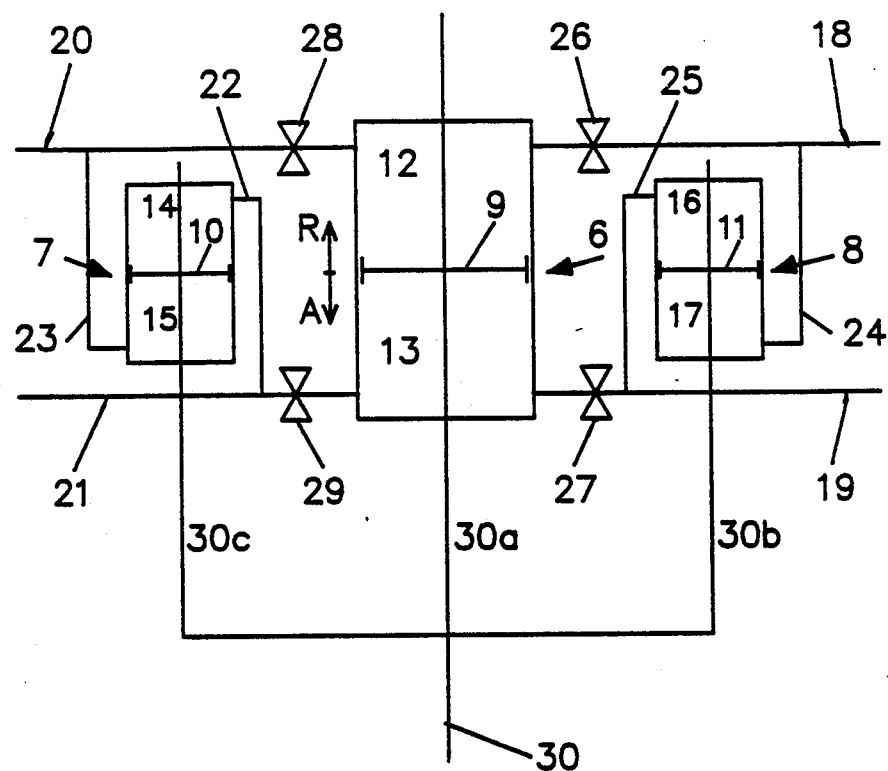
FIG. 6 schematically illustrates a second embodiment of the present invention.

According to a second preferred embodiment of the invention illustrated in FIG. 6, auxiliary pumps 7 and 8 are no longer disposed coaxially with main cylinder 6. The pistons are not driven by means of a single rod, but, for instance, by means of three rods 30a, 30b, 30c linked to a rod 30 which is driven in a rectilinear reciprocating motion by any known means familiar to one skilled in the art such as an electromagnetic motor.

In the case where, as illustrated in FIG. 6, the pumps 6, 7 and 8 are comprised of cylinders having a circular cross section, pistons 10 and 11 are preferably configured with a cross section having a surface area equal to half the surface area of the cross section of piston 9. Thus, when pistons 10 and 11 are driven with the same motion and the same amplitude as piston 9, the quantity of the liquid displaced in each of main chambers 12 and 13 is twice the quantity of liquid displaced simultaneously in each one of auxiliary chambers 14, 15, 16 and 17.

FIG. 6 illustrates, moreover, that the functions of the auxiliary chambers 15 and 17 may be reversed. In effect, according to this embodiment of the invention, chamber 15, complementary to chamber 14, is connected by a line 23 to aspiration line 20 for the first liquid. Auxiliary chamber 17, complementary to the auxiliary chamber 16, is connected by a line 24 to the delivery line 18 for the first liquid. In the same manner, it is possible to reverse the functions of the chambers 14 and 16 with respect to aspiration and delivery stages of each as compared to the embodiment of the invention illustrated in FIG. 3.

Figure 7:
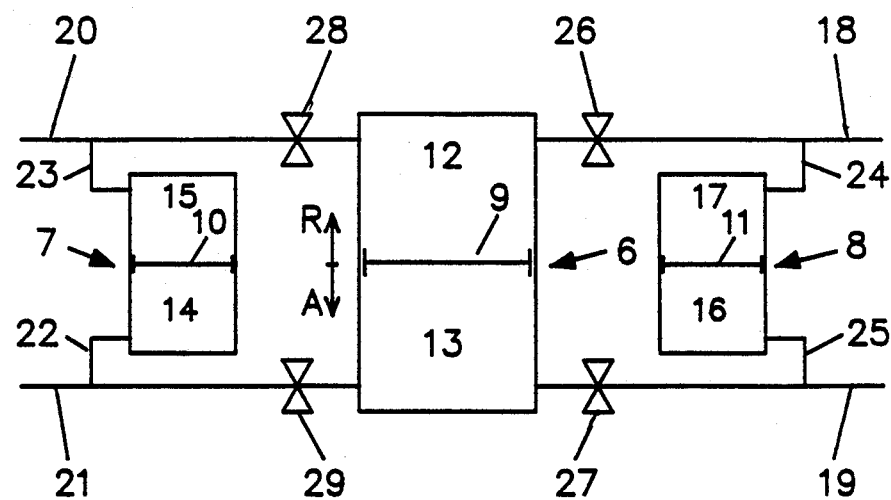
FIG. 7 schematically illustrates a third embodiment of the present invention.

The circuit diagram of FIG. 7 illustrates another relative arrangement of auxiliary chambers 14, 15, 16 and 17. In this case, auxiliary pistons 10 and 11 are displaced at the same time and with the same amplitude as piston 9, but in opposite directions. Thus, when main piston 9 is displaced in the direction of arrow A, auxiliary pistons 10 and 11 are displaced in the direction of arrow R and vice versa. This relative motion may be obtained, for instance, by means of mechanisms using crank connecting rod systems.

In the embodiment of FIG. 7, auxiliary chamber 14 is connected by a line 22 to delivery line 21, downstream from valve 29. Auxiliary chamber 15, which is complementary to auxiliary chamber 14, is connected by a line 23 to aspiration line 20 upstream from valve 28. Auxiliary chamber 16 is connected by a line 25 to aspiration line 19, upstream from valve 27, and auxiliary chamber 17, which is complementary with auxiliary chamber 16, is connected by a line 24 to delivery line 18. The operation of the device according to this mode of embodiment is as follows.

In the aspiration stage, valves 26 and 27 are closed and valves 28 and 29 are open. Main piston 9 is displaced in the direction of arrow A and auxiliary pistons 10 and 11 are displaced in the direction of arrow R.

The increase in volume of main chamber 12 entails aspiration of the first liquid into chamber 12, one-half of the first liquid entering chamber 12 coming from aspiration line 20, and one-half from chamber 15 via line 23. The simultaneous decrease in volume of main chamber 13 entails the delivery of an equal volume of the second liquid from chamber 13, one-half into chamber 14 via line 22 and one-half into the evacuation or regeneration means via line 21. Simultaneously, movement of the piston 11 in direction R delivers the first liquid from auxiliary chamber 17 into delivery line 18 via line 24 and draws the second liquid coming from the aspiration line 19 into auxiliary chamber 16 via line 25.

In the delivery stage, valves 26 and 27 are open and valves 28 and 29 are closed. Piston 9 is displaced in the direction of arrow R and pistons 10 and 11 are displaced in the direction of arrow A.

The first liquid which is expelled from main chamber 12 by piston 9 moving in direction R is delivered into auxiliary chamber 17 via line 24, and into delivery line 18. The increase in volume of main chamber 13 entails the aspiration of the second liquid into chamber 13, one-half of the volume of liquid entering chamber 13 coming from auxiliary chamber 16 via line 25, and one-half from aspiration line 19. Simultaneously, movement of the piston 10 in direction A entails delivery of the second liquid from auxiliary chamber 14 towards the delivery line 21 via line 22, as well as aspiration of the first liquid into the chamber 15 from aspiration line 20 via line 23.

The embodiment of the present invention illustrated in FIG. 7 makes it possible to pump equal quantities of a first and a second liquid while maintaining a continuous flow in aspiration lines 19 and 20, and in delivery lines 18 and 21.

Many variations of the embodiments described and illustrated are within the grasp of one skilled in the art without thereby departing from the scope of the present invention. Thus the drive means of the pistons may be mechanical drive, but may also be a magnetic, electromagnetic or hydraulic drive.

With reference to FIG. 3, in the case of a hydraulic drive, that is to say, by means of pumps for example, one pump may be disposed in aspiration line 20 for the first liquid upstream from the junction with line 23, and one pump may be disposed in aspiration line 19 for the second liquid upstream from the junction with line 25. In this arrangement pumping device 6 no longer performs a motor function for the pumping. It is also possible, while remaining within the scope of the present invention, to replace the pistons by leakproof membranes or diaphragms.

Valves 26, 27, 28 and 29 are preferably control valves, such as electrovalves. However, these valves need not be control valves but may be replaced by any type of conventional obturating device, such as one-way valves. However, when using one-way or check valves in combination with hydraulic drives, there would be the risk of the first liquid continuously passing from aspiration line 20 towards delivery line 18, and the further risk of the second liquid passing from aspiration line 19 towards delivery line 21. The set of four valves 26, 27, 28 and 29 may also be replaced by any equivalent means such as a distributor allowing a selection of the lines of passage for the dialysis liquid.

In the modes of embodiment represented in FIGS. 3, 6 and 7, a cylindrical shape with a circular cross section was adopted for the cylinder of pumps 6, 7 and 8, with the area of the cross section of main cylinder 40 being twice the area of the cross section of each of the auxiliary cylinders. It is, however, possible to choose a non-circular cross section for the auxiliary cylinders, and accordingly modify the amplitude of the movement of the auxiliary pistons so that the quantity of the liquid simultaneously displaced in each of the corresponding auxiliary chambers with displacement of auxiliary pistons 10 and 11 is one-half the quantity of liquid displaced in each main chamber by main piston 9.

It is also possible that one or more of the cylinders of pumps 6, 7 and 8 be divided into two complementary chambers by means of an equalizer system designed in such a way that the two associated chambers should be complementary to each other.

Among the possible applications of the method and of the apparatus according to the present invention, there has been described the pumping of equal quantities of a fresh dialysis liquid and of a used dialysis liquid, as illustrated with reference to FIG. 3.

However, the objects of the present invention may also be attained within the framework of haemofiltration with reinjection. In fact, in that technique, the quantity of the liquid withdrawn from the blood by ultrafiltration is replaced, save for the adjustment of the patient's weight, by an equal quantity of a substitution liquid which is injected into the blood. The first liquid pumped is then the ultrafiltrated liquid and the second liquid is the substitution liquid.

Additional advantages and modifications will readily occur to those skilled in the art. Therefore, the invention in its broader aspects is not limited to the specific details, representative devices, and illustrative examples shown and described. Accordingly, departures may be made from such details without departing from the spirit or scope of the general inventive concept as defined by the appended claims and their equivalents.

What is claimed is:

1. In an artificial kidney pumping system, a method for pumping a predetermined quantity of a first liquid from a source into a first discharge line outlet, and for pumping an equal quantity of a second liquid from a second intake line inlet into evacuation means, at a substantially constant flow, said pumping system including main reciprocating pump means having first and second complementary main chambers, wherein reciprocation of said main pump means displaces a substantially equal first volume from each of said main chambers; first auxiliary reciprocating pump means having first and second complementary auxiliary chambers, wherein reciprocation of said first auxiliary pump means displaces a substantially equal second volume from each of said first and second auxiliary chambers, said second volume being substantially equal to one half said first volume; and second auxiliary pump means having third and fourth complementary auxiliary chambers, wherein reciprocation of said second auxiliary pump means displaces a substantially equal third volume from each of said third and fourth auxiliary chambers, said third volume being substantially equal to one half said first volume, comprising the steps of:

reciprocating said main pump means and said first and second auxiliary pump means between a first and a second direction such that the volume of said first main chamber varies inversely with the volume of said second and fourth auxiliary chambers, and directly with the volume of said first and third auxiliary chambers;

aspirating said predetermined quantity of said first liquid into said first main chamber from both said fourth auxiliary chamber and from said source of said first liquid during reciprocation of said pump means in said first direction;

aspirating said quantity of said first liquid into said fourth auxiliary chamber from said source of said first liquid during reciprocation of said pump means in said second direction;

discharging said quantity of said first liquid into both said second auxiliary chamber and said first discharge line outlet during reciprocation of said pump means in said second direction;

discharging said quantity of said first liquid into said first discharge line outlet from said second auxiliary chamber during reciprocation of said pump means in said first direction;

aspirating said quantity of said second liquid into said second main chamber from both said second intake line inlet and said third auxiliary chamber during reciprocation of said pump means in said second direction;

aspirating said quantity of said second liquid into said third auxiliary chamber from said second intake line inlet during reciprocation of said pump means in said first direction;

discharging said quantity of said second liquid from discharging said quantity of said second liquid from said second main chamber into both said first auxiliary chamber and said evacuation means during reciprocation of said pump means in said first direction; and discharging said quantity of said second liquid into said evacuation means from said first auxiliary chamber during reciprocation of said pump means in said second direction whereby the same said quantity of first and second liquid flows through said first discharge line outlet and said second intake line inlet respectively, in a substantially constant flow during reciprocation of said pump means in both said first and said second direction.

2. The method of claim 1, wherein said first liquid is fresh dialysis liquid and said second liquid is used dialysis liquid.

3. The method of claim 1, wherein said first liquid is ultrafiltered liquid and said second liquid is a substitution liquid.

4. The method of claim 1, wherein said main pump means and said first and second auxiliary pump means reciprocate in unison between said first and second direction.

5. A method for pumping a predetermined quantity of a first liquid from a source into a hemodialyser of an artificial kidney, and for pumping an equal quantity of a second liquid into a regeneration means from the hemodialyser, at a substantially constant flow, said artificial kidney including main reciprocating pump means having first and second complementary main chambers of substantially equal volume, first auxiliary reciprocating pump means having first and second complementary auxiliary chambers of substantially equal volume, and second auxiliary pump means having third and fourth complementary auxiliary chambers of substantially equal volume, comprising the steps of:

reciprocating said main pump means and said first and second auxiliary pump means in unison between a first and a second direction such that the volume of said first main chamber varies inversely with the volume of said second and fourth auxiliary chambers, and directly with the volume of said first and third auxiliary chambers;

aspirating said predetermined quantity of said first liquid into said first main chamber from both said fourth auxiliary chamber and from said source of said first liquid during reciprocation of said pump means in said first direction;

aspirating said quantity of said first liquid into said fourth auxiliary chamber from said source of said first liquid during reciprocation of said pump means in said second direction;

discharging said quantity of said first liquid into both said second auxiliary chamber and said hemodialyser during reciprocation of said pump means in said second direction;

discharging said quantity of said first liquid into said hemodialyser from said second auxiliary chamber during reciprocation of said pump means in said first direction;

aspirating said quantity of said second liquid into said second main chamber from both said hemodialyser and said third auxiliary chamber during reciprocation of said pump means in said second direction;

aspirating said quantity of said second liquid into said third auxiliary chamber from said hemodialyser during reciprocation of said pump means in said first direction;

discharging said quantity of said second liquid from said second main chamber into both said first auxiliary chamber and said regeneration means during reciprocation of said pump means in said first direction; and discharging said quantity of said second liquid into said regeneration means from said first auxiliary chamber during reciprocation of said pump means in said second direction whereby the same said quantity of first and second liquid is aspirated into and discharged from said hemodialyser in a substantially constant flow during reciprocation of said pump means in both said first and said second direction.

6. The method of claim 5, wherein said first liquid is fresh dialysis liquid and said second liquid is used dialysis liquid.

7. The method of claim 5, wherein said first liquid is ultrafiltered liquid and said second liquid is a substitution liquid.

8. An artificial kidney pumping system for pumping a predetermined quantity of a first liquid from a source through a first discharge line outlet, and for pumping an equal quantity of a second liquid from a second intake line inlet into evacuation means, at a substantially constant flow, comprising:

main reciprocating pump means having first and second complementary main chambers, wherein reciprocation of said main pump means displaces a substantially equal first volume from each of said main chambers;

first auxiliary reciprocating pump means having first and second complementary auxiliary chambers, wherein reciprocation of said first auxiliary pump means displaces a substantially equal second volume from each of said first and second auxiliary chambers, said second volume being substantially equal to one half said first volume;

second auxiliary pump means having third and fourth complementary auxiliary chambers, wherein reciprocation of said second auxiliary pump means displaces a substantially equal third volume from each of said third and fourth auxiliary chambers, said third volume being substantially equal to one half said first volume;

drive means for reciprocating said main pump means and said first and second auxiliary pump means between a first and a second direction such that the volume of said first main chamber varies inversely with the volume of said second and fourth auxiliary chambers, and directly with the volume of said first and third auxiliary chambers;

first intake line means for aspirating said predetermined quantity of said first liquid into said first main chamber from both said fourth auxiliary chamber and from said source of said first liquid during reciprocation of said pump means in said first direction, and for aspirating said quantity of said first liquid into said fourth auxiliary chamber from said source of said first liquid during reciprocation of said pump means in said second direction;

first discharge line means for discharging said quantity of said first liquid into both said second auxiliary chamber and said first discharge line outlet during reciprocation of said pump means in said second direction, and for discharging said quantity of said first liquid into said first discharge line outlet from said second auxiliary chamber during reciprocation of said pump means in said first direction;

second intake line means for aspirating said quantity of said second liquid into said second main chamber from both said second intake line inlet and said third auxiliary chamber during reciprocation of said pump means in said second direction, and for aspirating said quantity of said second liquid into said third auxiliary chamber from said second intake line inlet during reciprocation of said pump means in said first direction;

second discharge line means for discharging said quantity of said second liquid from said second main chamber into both said first auxiliary chamber and said evacuation means during reciprocation of said pump means in said first direction, and for discharging said quantity of said second liquid into said evacuation means from said first auxiliary chamber during reciprocation of said pump means in said second direction wherein the same said quantity of first and second liquid flows through said first discharge line outlet and said second intake line inlet, respectively, in a substantially constant flow during reciprocation of said pump means in both said first and second direction.

9. The system of claim 8, wherein said first intake line means comprises a first conduit connecting said source of first liquid to said first main chamber, a first valve means, disposed in said first conduit, for selectively interrupting flow through said first conduit, and a second conduit connecting said fourth auxiliary chamber to said first conduit upstream of said first valve means; said first discharge line means comprises a third conduit connecting said first main chamber to said first discharge line outlet, a second valve means, disposed in said third conduit, for selectively interrupting flow through said third conduit, and a fourth conduit connecting said second auxiliary chamber to said third conduit downstream of said second valve means;

said second intake line means comprises a fifth conduit connecting said second intake line inlet to said second main chamber, a third valve means, disposed in said fifth conduit, for selectively interrupting flow through said fifth conduit, and a sixth conduit connecting said third auxiliary chamber to said fifth conduit upstream of said third valve means; and said second discharge line means comprises a seventh conduit connecting said second main chamber to said evacuation means, a fourth valve means, disposed in said seventh conduit, for selectively interrupting flow through said seventh conduit, and an eighth conduit connecting said first auxiliary chamber to said seventh conduit downstream of said fourth valve means.

10. The system of claim 9, including means for selectively operating said first, second, third, and fourth valve means between an open and a closed position in accordance with the direction of movement of said pump means in said first and second directions.

11. The system of claim 9, wherein said first, second, third, and fourth valve means each comprise a control valve.

12. The system of claim 9, wherein said first, second, third, and fourth valve means are disposed within a distributor.

13. The system of claim 8, wherein said main pump means and each said first and second auxiliary pump means comprise a respective housing and respective pistons disposed therein, each said piston dividing each respective housing into said respective main and auxiliary complementary chambers.

14. The system of claim 13, wherein said drive means includes a rod, said pistons being coaxially disposed on said rod, and means for moving said rod and said pistons disposed thereon in a reciprocating motion to thereby vary the volume in said main and auxiliary chambers as said pistons are reciprocated in respective housings.

15. The system of claim 14, wherein each said housing of said main pump means and said first and second auxiliary pump means has a circular cross-section.

16. The system of claim 8, wherein said main pump means and each said first and second auxiliary pump means comprises a housing having a diaphragm disposed therein to define the respective complementary main and auxiliary chambers.

17. The system of claim 8, wherein said drive means includes an electromagnetic motor.

18. The system of claim 8, wherein said drive means includes means for mechanically reciprocating said main and auxiliary pump means.

19. The system of claim 8, wherein the cross-sectional area of each said main chamber is twice the cross-sectional area of each said auxiliary chamber.

20. The system of claim 8, wherein said main pump means and said first and second auxiliary pump means reciprocate in unison between said first and second direction.

21. The system of claim 8, wherein said first and second main chambers have equal volumes and said auxiliary chambers each have volumes equal to one half the volume of each of said main chambers.

* * * * *

UNITED STATES PATENT AND TRADEMARK OFFICE
CERTIFICATE OF CORRECTION

PATENT NO.  : 4,857,199

DATED       : August 15, 1989

INVENTOR(S) : JEAN-LOUP CORTIAL

It is certified that error appears in the above-identified patent and that said Letters Patent is hereby corrected as shown below:

Claim 1, column 11, line 34, delete "discharging said quantity of said second liquid from".

Signed and Sealed this

Fourth Day of December, 1990

Attest:

HARRY F. MANBECK, JR.

*Attesting Officer*          *Commissioner of Patents and Trademarks*